US008962861B2

(12) United States Patent
Shih et al.

(10) Patent No.: US 8,962,861 B2
(45) Date of Patent: Feb. 24, 2015

(54) CATALYST COMPOSITION AND METHOD FOR PREPARING AMIDE

(75) Inventors: Chien-Chuan Shih, Taipei (TW); Cheng-Fa Hsieh, Taipei (TW); Hung-Hung Hseuh, Taipei (TW); Tung-Han Tsai, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 124 days.

(21) Appl. No.: 13/359,851

(22) Filed: Jan. 27, 2012

(65) Prior Publication Data

US 2013/0053575 A1    Feb. 28, 2013

(30) Foreign Application Priority Data

Aug. 26, 2011 (TW) .............................. 100130628 A

(51) Int. Cl.
*C07D 233/58* (2006.01)
*B01J 31/02* (2006.01)

(52) U.S. Cl.
CPC ........... *B01J 31/0239* (2013.01); *C07D 233/58* (2013.01); *B01J 31/0244* (2013.01); *B01J 2231/52* (2013.01)
USPC ..................................................... 548/335.1

(58) Field of Classification Search
USPC ..................................................... 548/335.1
See application file for complete search history.

(56) References Cited

U.S. PATENT DOCUMENTS 6,265,574 B1    7/2001    Kitamura et al.

FOREIGN PATENT DOCUMENTS

| CN | 1852898 A | 10/2006 |
|---|---|---|
| CN | 1919834 A | 2/2007 |
| WO | 2008/145312 A1 | 12/2008 |

OTHER PUBLICATIONS

Ganzha et al., Russian Journal of Organic Chemistry, 2006, vol. 2, No. 8, pp. 1248-1249.*
Ding et al., Jhejiang Gongye Daxue Xuebao (2005), 33(1), 93-95, Abstract only.*

* cited by examiner

*Primary Examiner* — Rebecca Anderson
(74) *Attorney, Agent, or Firm* — Mintz Levin Cohn Ferris Glovsky and Popeo, P.C.; Peter F. Corless; Richard B. Emmons

(57) ABSTRACT

The present invention provides a catalyst composition and a method for preparing an amide. The catalyst composition of the present invention including a hydroxylamine salt, sulfuric acid, and a nitrogen-containing heterocyclic compound is used for catalyzing a ketoxime to form an amide in the Beckman rearrangement reaction. The preparation of an amide by using the catalyst composition of the present invention has high conversion rate of a ketoxime, high selectivity of an amide and high tolerance to water.

18 Claims, No Drawings

CATALYST COMPOSITION AND METHOD FOR PREPARING AMIDE

CROSS-REFERENCES TO RELATED APPLICATIONS

This application claims under 35 U.S.C. §119(a) the benefit of Taiwanese Application No. 100130628, filed Aug. 26, 2011, the entire contents of which is incorporated herein by reference.

BACKGROUND OF THE INVENTION

1. Field of the Invention

The present invention relates to methods for preparing amides, and more particularly, to a method for separating an amide from a ketoxime.

2. Description of the Prior Art

Caprolactam is an important raw material in the manufacture of nylon 6 fibers and thin films. Beckman rearrangement of cyclohexanone oxime is an important reaction step in producing caprolactam. Currently, oleum is used as a catalyst for converting cyclohexanone oxime to caprolactam sulfate during Beckman rearrangement, and then ammonia is used for neutralization, so as to obtain caprolactam. While the conversion rate of cyclohexanone oxime is almost 100% and the selectivity for caprolactam is 99%, a large amount of low-valued ammonium sulfate is generated during the reaction, and concentrated sulfuric acid used for catalysis causes problems such as corrosion to the whole equipment and environmental pollution. In the recent years, researches on new production technologies of caprolactam focus on reducing or avoiding the generation of the by-product, ammonium sulfate. U.S. Pat. No. 6,265,574 discloses that the molecular sieve is used as the catalyst for a gaseous phase Beckmann rearrangement reaction in a fluidized bed system. In this method, no by-product, ammonium sulfate, is formed in the gaseous reaction; however, the selectivity of caprolactam is only 95.7%, and the operation temperature (300 to 350° C.) is higher than that of a liquid phase reaction. In addition, the catalyst in the gaseous reaction is easily inactive, and the regeneration is frequently performed, such that the catalyst cannot be used for the long term operation.

Moreover, in comparison with the gaseous phase reaction, the liquid-phase rearrangement has advantages including moderate reaction conditions, fewer requirements to the equipments, etc., and is advantageous to the reconstruction of the current equipments. As a result, scholars worldwide have put efforts on developing liquid-phase rearrangement, and attained substantial developments and breakthrough. For example, in Chinese Patent No. 1852898A assigned to Sumitomo Chemical Company Ltd. in Japan, an ionic liquid having the sulfonate group is used as a catalyst to obtain the selectivity of caprolactam up to 99%. In Chinese Patent No. 1919834 assigned to Lanzhou Institute of Chemical Physics in China, an ionic liquid having sulfuryl chloride is used as a catalyst to obtain the selectivity of caprolactam up to 97.2%. In WO2008/145312A1 assigned to DSM N.V. in Netherlands, an anionic solution having sulfate is used for conversion reaction to obtain the selectivity of amide up to 99%.

However, the above-mentioned catalysts cannot be regenerated for multiple times. The water content of the catalyst composition is too high, and the cyclohexanone oxime is hydrolyzed to cyclohexanone, such that the selectivity is decreased. The water needs to be removed before the regeneration of the catalyst composition.

Hence, there is a need to develop a catalyst composition for enhancing the tolerance to water, the conversion rate of cyclohhexanone oxime and the selectivity of the amide in the preparation of an amide.

SUMMARY OF THE INVENTION

The present invention provides a catalyst composition for catalyzing a ketoxime to form an amide in Beckman rearrangement reaction. The catalyst composition includes a hydroxylamine salt; sulfuric acid; and a nitrogen-containing heterocyclic compound. In the embodiment, the nitrogen-containing heterocyclic compound is one or more selected from the group consisting of a compound of formula (I), a compound of formula (II) and a combination thereof:

wherein in the formula (I) and the formula (II), each circle is one of 5-membered to 10-membered rings and has one or more nitrogen atoms, and R1 and R2 are independently hydrogen or $C_1$-$C_8$alkyl, in which $C_1$-$C_8$alkyl is unsubstituted or substituted —OH, —COOH, $NH_2C(=NH)NH—$, —$NH_2$, —$CONH_2$, —COOR, wherein R is $C_1$-$C_8$alkyl, —$SO_3H$, ClSO—, hydroxylphenyl, $C_1$-$C_8$alkylthio, —SH, $C_6$-$C_{10}$phenyl or a 5-membered to 10-membered heteroaryl.

The hydroxylamine salt is an acidic hydroxylamine salt. The acidic hydroxylamine salt may be one or more selected from the group consisting of hydroxylamine sulfate, hydroxylamine hydrochloride, hydroxylamine nitrate and hydroxylamine phosphate.

The present invention further provides a method for preparing an amide, including the step of providing a catalyst composition having a hydroxylamine salt, sulfuric acid, and a nitrogen-containing heterocyclic compound to catalyze a ketoxime to form an amide in Beckman rearrangement reaction.

The catalyst composition of the present invention includes a hydroxylamine salt; sulfuric acid; and a nitrogen-containing heterocyclic compound. In comparison with the conventional catalyst having an acidic ion liquid, the catalyst composition of the present invention has more tolerance to water, higher conversion rate of a ketoxime in the rearrangement reaction and higher selectivity of an amide. Further, in the present invention, the Beckman rearrangement reaction is performed at a low temperature (about 60 to 150° C.), such that the catalyst composition may be easily regenerated, and be used for the large-scale production in the industry.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides a method for separating an amide from an amino acid ionic liquid in Beckman rearrangement reaction, and the method includes the step of providing a polar solvent and an extracting agent to the amino acid ionic liquid, so as to separate the amide from the amino acid ionic liquid.

The present invention provides a catalyst composition for preparing an amide. The catalyst composition includes a hydroxylamine salt; sulfuric acid; and a nitrogen-containing heterocyclic compound.

In the present invention, the hydroxylamine salt is an acidic hydroxylamine salt. The acidic hydroxylamine salt may be one or more selected from the group consisting of hydroxylamine sulfate, hydroxylamine hydrochloride, hydroxylamine nitrate and hydroxylamine phosphate. In one embodiment, the hydroxylamine salt is hydroxylamine sulfate. The molar ratio of the hydroxylamine salt to the ketoxime is in a range of from 0.001:1 to 0.05:1, preferably 0.005:1 to 0.05:1, and more preferably 0.01:1 to 0.05:1.

In one embodiment, the nitrogen-containing heterocyclic compound is one or more selected from the group consisting of a compound of formula (I), a compound of formula (II) and a combination thereof:

wherein in the formula (I) and the formula (II), each circle is one of 5-membered to 10-membered rings and has one or more nitrogen atoms, and R1 and R2 are independently hydrogen or $C_1$-$C_8$alkyl, in which $C_1$-$C_8$alkyl is unsubstituted or substituted —OH, —COOH, $NH_2C(=NH)NH$—, —$NH_2$, —$CONH_2$, —COOR, wherein R is $C_1$-$C_8$alkyl, —$SO_3H$, ClSO—, hydroxylphenyl, $C_1$-$C_8$alkylthio, —SH, $C_6$-$C_{10}$phenyl or a 5-membered to 10-membered heteroaryl.

In the present invention, $C_{1-8}$alkyl is a linear, branched or circular alkyl. The $C_{1-8}$alkyl may be, but not limited to, methyl, ethyl, propyl, isopropyl, butyl, sec-butyl, pentyl, hexyl or cyclohexyl. Preferably, the $C_{1-8}$alkyl is methyl, ethyl, propyl, butyl or pentyl.

The nitrogen-containing compound may be a 5-membered to 10-membered heteroaryl, and have one or two nitrogen atoms. For example, the nitrogen-containing compound is one or more selected from the group consisting of N-methylimidazole, pyridine, piperidine and pyrrolidine.

In the present invention, when the catalyst composition is arranged or cycled to the reactor, the molar ratio of the hydroxylamine salt to the sulfuric acid is in a range of from 0.00022:1 to 0.011:1; the molar ratio of the hydroxylamine salt to the nitrogen-containing compound is in a range of from 0.00044:1 to 0.022:1; and the molar ratio of the nitrogen-containing compound to the sulfuric acid is 1:2.

The present invention further provides a method for preparing an amide, including the step of providing the catalyst composition of the present invention to catalyze a ketoxime to form an amide in the Beckman rearrangement reaction.

In the present invention, the ketoxime is acetone oxime, butanone oxime, diphenylketone oxime, acetophenone oxime, cyclopentanone oxime, cyclohexanone oxime, cycloheptanone oxime, cyclooctanone oxime or cyclododecanone oxime.

Generally, the Beckman rearrangement reaction using the catalyst composition for catalyzing a ketoxime to form an amide in a solvent such as water is performed at 60 to 150° C., preferably 80 to 130° C., and more preferably 90 to 120° C., for 0.1 to 10 hours, preferably 0.5 to 3 hours, and more preferably 0.5 to 1 hour.

In the present invention, the molar ratio of the hydroxylamine salt to the ketoxime is in a range of from 0.001:1 to 0.05:1, preferably 0.005:1 to 0.05:1, and more preferably 0.01:1 to 0.05:1.

In the present invention, the conversion rate of the ketoxime is almost 100%, the selectivity of caprolactam is 99.1%, and the tolerance to water is high in the preparation of an amide. Therefore, the reaction activity is outstanding in the Beckman rearrangement reaction by using the catalyst composition of the present invention for catalyzing a ketoxime to form an amide.

The following embodiments are used for illustrating features and advantages of the present invention, but not limiting the scope of the present invention.

EMBODIMENTS

The present invention is illustrated by, but not limited to, the following embodiments. Ketoximes and amides were measured by gas chromatography. The conversion rate of ketoximes and selectivity of amides were calculated by the following equations.

Conversion rate (%)=(mole number of consumed ketoxime/initial mole number of ketoxime (%)]×100%

Selectivity (%)=[mole number of the produced amide/mole number of consumed ketoxime (%)]×100%

The extract efficiency of amides was calculated by the following equation.

Extract efficiency (%)=[mole number of the extracted amide/mole number of amide]×100%

Embodiment 1

0.1 mole of methylimidazole, 0.2 mole of sulfuric acid and 0.0005 mole of hydroxylamine sulfate were added in a round-bottom flask. The water content of the catalyst composition was 1%, the mixture was stirred and heated to 110° C., and then mixed with 0.05 mole of ketoxime to perform the Beckman rearrangement reaction. After performing the reaction for 0.5 hour, the conversion rate of the ketoxime and the selectivity of the amide were measured by gas chromatography. The results were shown in Table 1.

TABLE 1

| Embodiment | Water content of catalyst composition | Conversion rate of ketoxime | Selectivity of amide |
|---|---|---|---|
| 1 | 1% | 100% | 98.7% |

Comparative Example 1

0.1 mole of methylimidazole and 0.2 mole of sulfuric acid were added in a round-bottom flask. The water content of the catalyst composition was 1%, the mixture was stirred and heated to 110° C., and then mixed with 0.05 mole of ketoxime to perform the Beckman rearrangement reaction After performing the reaction for 0.5 hour, the conversion rate of the ketoxime and the selectivity of the amide were measured by gas chromatography. The results were shown in Table 2.

TABLE 2

| Comparative Example | Water content of catalyst composition | Conversion rate of ketoxime | Selectivity of amide |
|---|---|---|---|
| 1 | 1% | 100% | 95.3% |

Embodiments 2-5

0.1 mole of methylimidazole, 0.2 mole of sulfuric acid and the specific amount of hydroxylamine sulfate were added in a round-bottom flask. The water content of the catalyst composition was 1%, the mixture was stirred and heated to 110° C., and then mixed with 0.05 mole of ketoxime to perform the Beckman rearrangement reaction. After performing the reaction for 0.5 hour, the conversion rate of the ketoxime and the selectivity of the amide were measured by gas chromatography. The results were shown in Table 3.

TABLE 3

| Embodiment | Amount of hydroxylamine sulfate (mole) | Conversion rate of ketoxime | Selectivity of amide |
|---|---|---|---|
| 2 | 0.00025 | 100% | 98.7% |
| 3 | 0.0005 | 100% | 98.7% |
| 4 | 0.001 | 100% | 99% |
| 5 | 0.002 | 100% | 99% |

Embodiments 6-9

0.1 mole of methylimidazole, 0.2 mole of sulfuric acid and 0.0005 mole of hydroxylamine sulfate were added in a round-bottom flask. In the presence of the specific water content of the catalyst composition, the mixture was stirred and heated to 110° C., and then mixed with 0.05 mole of ketoxime to perform the Beckman rearrangement reaction. After performing the reaction for 0.5 hour, the conversion rate of the ketoxime and the selectivity of the amide were measured by gas chromatography. The results were shown in Table 4.

TABLE 4

| Embodiment | Water content of catalyst composition | Conversion rate of ketoxime | Selectivity of amide |
|---|---|---|---|
| 6 | 0.28% | 100% | 99.1% |
| 7 | 0.5% | 100% | 99.1% |
| 8 | 0.1% | 100% | 98.7% |
| 9 | 2% | 100% | 97.9% |

Comparative Examples 2-5

0.1 mole of methylimidazole and 0.2 mole of sulfuric acid were added in a round-bottom flask. In the presence of the specific water content of the catalyst composition, the mixture was stirred and heated to 110° C., and then mixed with 0.05 mole of ketoxime to perform the Beckman rearrangement reaction. After performing the reaction for 0.5 hour, the conversion rate of the ketoxime and the selectivity of the amide were measured by gas chromatography. The results were shown in Table 5.

TABLE 5

| Comparative Example | Water content of catalyst composition | Conversion rate of ketoxime | Selectivity of amide |
|---|---|---|---|
| 2 | 0.15% | 100% | 98.1% |
| 3 | 0.2% | 100% | 97.8% |
| 4 | 0.3% | 100% | 97.6% |
| 5 | 0.45% | 100% | 96.4% |

Embodiments 10-12

0.1 mole of methylimidazole, 0.2 mole of sulfuric acid and 0.0005 mole of the specific hydroxylamine salt were added in a round-bottom flask. The water content of the catalyst composition was 1%, the mixture was stirred and heated to 110° C., and then mixed with 0.05 mole of ketoxime to perform the Beckman rearrangement reaction. After performing the reaction for 0.5 hour, the conversion rate of the ketoxime and the selectivity of the amide were measured by gas chromatography. The results were shown in Table 6.

TABLE 6

| Embodiment | Hydroxylamine salt | Conversion rate of ketoxime | Selectivity of amide |
|---|---|---|---|
| 10 | hydroxylamine sulfate | 100% | 98.7% |
| 11 | hydroxylamine hydrochloride | 100% | 98.8% |
| 12 | hydroxylamine phosphate | 100% | 98.6% |

Accordingly, the preparation of an amide by using the catalyst composition of the present invention has high conversion rate of the ketoxime and high selectivity of the amide. The molar ratio of hydroxylamine sulfate to ketoxime in a range of from 0.01:1 to 0.05:1 results in the best conversion rate and selectivity. Moreover, the catalyst composition of the present invention improves the tolerance to water in the Beckman rearrangement reaction, so as to increase the production yield.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A composition for a Beckman rearrangement reaction, comprising:
   a ketoxime for forming an amide;
   a hydroxylamine salt;
   sulfuric acid; and
   a nitrogen-containing heterocyclic compound.

2. The composition of claim 1, wherein the nitrogen-containing heterocyclic compound is one or more selected from the group consisting of a compound of formula (I), a compound of formula (II) and a combination thereof:

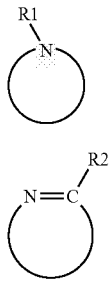

(I)

(II)

wherein in the formula (I) and the formula (II), each circle is one of 5-membered to 10-membered rings and has one or more nitrogen atoms, and R1 and R2 are independently hydrogen or $C_1$-$C_8$alkyl, in which $C_1$-$C_8$alkyl is unsubstituted or substituted —OH, —COOH, $NH_2C$(=NH)NH—, —$NH_2$, —$CONH_2$, —COOR, wherein R is $C_1$-$C_8$alkyl, —$SO_3H$, ClSO—, hydroxylphenyl, $C_1$-$C_8$alkylthio, —SH, $C_6$-$C_{10}$phenyl or a 5-membered to 10-membered heteroaryl.

3. The composition of claim 1, wherein the hydroxylamine salt is an acidic hydroxylamine salt.

4. The composition of claim 3, wherein the acidic hydroxylamine salt includes one or more selected from the group consisting of hydroxylamine sulfate, hydroxylamine hydrochloride, hydroxylamine nitrate and hydroxylamine phosphate.

5. The composition of claim 1, wherein a molar ratio of the hydroxylamine salt to the sulfuric acid is in a range of from 0.00022:1 to 0.011:1; a mole ratio of the hydroxylamine salt to the nitrogen-containing heterocyclic compound is in a range of from 0.00044:1 to 0.022:1; and a molar ratio of the nitrogen-containing compound to the sulfuric acid is 1:2.

6. The composition of claim 1, wherein the nitrogen-containing heterocyclic compound is one or more selected from the group consisting of N-methylimidazole, pyridine, piperidine and pyrrolidine.

7. A method for preparing an amide, comprising the step of:
providing a catalyst composition having a hydroxylamine salt, sulfuric acid, and a nitrogen-containing heterocyclic compound to catalyze a ketoxime to form an amide in Beckman rearrangement reaction.

8. The method of claim 7, wherein the nitrogen-containing heterocyclic compound is one or more selected from the group consisting of a compound of formula (I), a compound of formula (II) and a combination thereof:

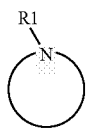

(I)

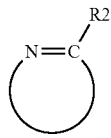

(II)

wherein in the formula (I) and the formula (II), each circle is one of 5-membered to 10-membered rings and has one or more nitrogen atoms, and R1 and R2 are independently hydrogen or $C_1$-$C_8$alkyl, in which $C_1$-$C_8$alkyl is unsubstituted or substituted —OH, —COOH, $NH_2C$(=NH)NH—, —$NH_2$, —$CONH_2$, —COOR, wherein R is C1-C8alkyl, —$SO_3H$, ClSO—, hydroxylphenyl, $C_1$-$C_8$alkylthio, —SH, $C_6$-$C_{10}$phenyl or a 5-membered to 10-membered heteroaryl.

9. The method of claim 7, wherein the hydroxylamine salt is an acidic hydroxylamine salt.

10. The method of claim 9, wherein the acidic hydroxylamine salt includes one or more selected from the group consisting of hydroxylamine sulfate, hydroxylamine hydrochloride, hydroxylamine nitrate and hydroxylamine phosphate.

11. The method of claim 7, wherein a molar ratio of the hydroxylamine salt to the ketoxime is in a range of from 0.001:1 to 0.05:1.

12. The method of claim 11, wherein the molar ratio of the hydroxylamine salt to the ketoxime is in a range of from 0.01:1 to 0.05:1.

13. The method of claim 7, wherein a molar ratio of the hydroxylamine salt to the sulfuric acid is in a range of from 0.00022:1 to 0.011:1; a molar ratio of the hydroxylamine salt to the nitrogen-containing heterocyclic compound is in a range of from 0.00044:1 to 0.022:1; and a molar ratio of the nitrogen-containing compound to the sulfuric acid is 1:2.

14. The method of claim 7, wherein the nitrogen-containing heterocyclic compound is one or more selected from the group consisting of N-methylimidazole, pyridine, piperidine and pyrrolidine.

15. The method of claim 7, wherein the ketoxime is acetone oxime, butanone oxime, diphenylketone oxime, acetophenone oxime, cyclopentanone oxime, cyclohexanone oxime, cycloheptanone oxime, cyclooctanone oxime or cyclododecanone oxime.

16. The method of claim 7, wherein the Beckman rearrangement reaction is performed at 60 to 150° C. for 0.1 to 10 hours.

17. The composition of claim 1, wherein a molar ratio of the hydroxylamine salt to the ketoxime is in a range of from 0.001:1 to 0.05:1.

18. The composition of claim 17, wherein the molar ratio of the hydroxylamine salt to the ketoxime is in a range of from 0.01:1 to 0.05:1.

* * * * *